(12) United States Patent
Shiina et al.

(10) Patent No.: US 7,601,538 B2
(45) Date of Patent: Oct. 13, 2009

(54) METHOD FOR ANALYZING IMPURITY

(75) Inventors: Yoshikazu Shiina, Tokyo (JP); Mohammad B. Shabani, Tokyo (JP)

(73) Assignee: Sumco Corporation, Tokyo (JP)

( * ) Notice: Subject to any disclaimer, the term of this patent is extended or adjusted under 35 U.S.C. 154(b) by 645 days.

(21) Appl. No.: 11/134,511

(22) Filed: May 23, 2005

(65) Prior Publication Data

US 2006/0003455 A1    Jan. 5, 2006

(30) Foreign Application Priority Data

May 24, 2004    (JP)    ............................ P2004-153713

(51) Int. Cl.
*G01N 31/00*    (2006.01)

(52) U.S. Cl. .............................. 436/6; 436/5

(58) Field of Classification Search ...................... 436/6, 436/80; 356/36; 438/16, 14; 134/3, 2
See application file for complete search history.

(56) References Cited

U.S. PATENT DOCUMENTS

| | | | | |
|---|---|---|---|---|
| 5,643,404 | A | * | 7/1997 | Muraoka et al. ............... 438/16 |
| 5,810,940 | A | * | 9/1998 | Fukazawa et al. .............. 134/3 |
| 5,913,980 | A | * | 6/1999 | Bathey ........................... 134/2 |
| 6,174,740 | B1 | * | 1/2001 | Ohta et al. ..................... 438/14 |
| 2004/0248311 | A1 | * | 12/2004 | Mohammad et al. .......... 436/80 |

FOREIGN PATENT DOCUMENTS

| JP | 07-130808 | 5/1995 |
|---|---|---|
| JP | 11-330043 | 11/1999 |
| JP | 2000-035424 | 2/2000 |

OTHER PUBLICATIONS

Machine Translation of JP 11-330043, Masaki, Evaluation of Silicon Wafer, 1999.*

* cited by examiner

*Primary Examiner*—Walter D Griffin
*Assistant Examiner*—Christine T Mui
(74) *Attorney, Agent, or Firm*—Pillsbury Winthrop Shaw Pittman, LLP

(57) ABSTRACT

This method for analyzing impurity includes: a step of immersing each of sets of two evaluation silicon wafers into a washing solution, thereby contaminating the evaluation silicon wafers to be in a same state of contamination; a step of dissolving each of a surface layer portion of either one of the evaluation silicon wafers and a bulk portion of the other evaluation silicon wafer with solutions including hydrofluoric acid respectively, and measuring a concentration of impurities included in each of the solutions; a step of determining a calibration curve that shows a relation between the concentrations of the impurities in the surface layer portions and the concentrations of the impurities in the bulk portions of the evaluation silicon wafers; a step of dissolving a surface layer portion of a silicon wafer of a test object with a solution including hydrofluoric acid, and measuring a concentration of impurities included in the solution; and a step of determining a concentration of impurities in a bulk portion based on the calibration curve using the measured concentration of the impurities.

4 Claims, 1 Drawing Sheet

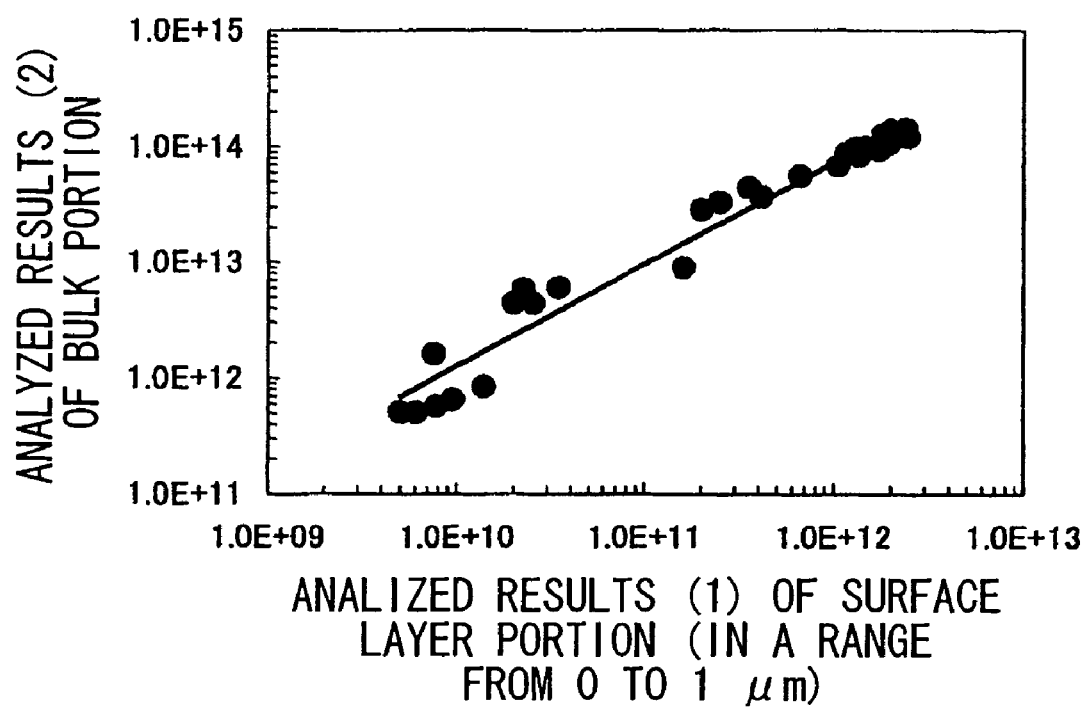

METHOD FOR ANALYZING IMPURITY

BACKGROUND OF THE INVENTION

1. Field of the Invention

The present invention relates to a method for analyzing impurities, and specifically, relates to a method for analyzing impurities to analyze impurities present in a silicon wafer.

This application claims priority from Japanese Patent Application No. 2004-153713 filed on May 24, 2004, the content of which is incorporated herein by reference.

2. Description of Related Art

In recent years, there have been demands for even greater degrees of flatness in silicon wafers. Therefore, there have also been demands for even greater degrees of flatness in a etching process. In this etching process for planarizing a silicon wafer, an alkaline etching solution is often used which is able to obtain an etched surface more excellent in flatness than that obtained by an acid etching solution. For example, a potassium hydroxide (KOH) solution or a sodium hydroxide (NaOH) solution is often used as the alkaline etching solution. However, a minute quantity of impurities are present in the KOH or NaOH solution, regardless of a concentration of the impurities. Examples of such impurities include Ni. This Ni has a tendency to be easily diffused into a silicon layer. Namely, when a silicon wafer is subjected to an alkaline etching, Ni diffuses from the silicon layer of the surface. As a result, the silicon wafer is contaminated by Ni.

When the silicon wafer is contaminated by Ni, the Ni is located at a particularly high concentration in a region from a surface of the silicon wafer to 1 μm in a depth direction. Ni concentration is lowered as a depth increases. Moreover, when a Ni-diffused silicon wafer is subjected to a heat treatment after the alkaline etching, the diffusion of Ni into bulk portions of the silicon wafer progresses even further.

When the bulk portions of the silicon wafer are contaminated by Ni, a problem arises in which for example, a gate oxide integrity in the device is degraded so that performance of the device is deteriorated. Accordingly, Ni contamination of the silicon wafer is a serious problem. Therefore, a method for analyzing impurities is required so as to confirm a degree of Ni contamination in the bulk portions of the silicon wafer.

Examples of the methods for analyzing impurities in the silicon wafer include total reflection x-ray fluorescence (TXRD), secondary ion mass spectrometry (SIMS), atomic absorption spectroscopy (AAS), and inductively coupled plasma mass spectrometry (ICP-MS).

A concrete example of a method for evaluating a degree of Ni contamination in a silicon wafer using the above analytical methods is a method for analyzing impurities in a surface of the wafer disclosed in Patent Document 1. In this Patent Document, a composition of a liquid mixture of hydrofluoric acid and nitric acid is adjusted in response to a distribution state of the impurities. The adjusted liquid mixture is supplied to the surface of the silicon wafer, and then after a predetermined time, the liquid mixture is recovered and concentrated, and analysis is then performed.

In a method for analyzing impurities in a silicon substrate and in a vapor phase thereof disclosed in Patent Document 2, a sample of a whole silicon wafer or a sample including a portion extending from a front surface to a rear surface of the silicon wafer which is cleaved, and a dissolving solution of a mixture of hydrofluoric acid, nitric acid, and sulfuric acid are set in a sealed reactor vessel such that the dissolving solution for silicon does not make contact with the sample. Then the solution is vaporized without the reactor vessel being heated or pressurized. As a result, the silicon wafer is dissolved by the vaporized solution. Subsequently, a dissolved liquid is recovered, and analysis of the impurities therein is performed.

Furthermore, in a method for evaluating a silicon wafer disclosed in Patent Document 3, observation of a surface state after etching and analysis of impurities are performed using an alkaline etching solution.

When using the method disclosed in Patent Document 1 alone, impurities in a surface layer of the silicon wafer can be analyzed, however impurities in a whole silicon bulk cannot be analyzed.

Moreover, in the method disclosed in Patent Document 2, great deal of time is required in order to dissolve the silicon wafer. In addition, a large quantity of acid is used in order to dissolve the silicon wafer so that a cost of chemical solutions used is expensive.

Furthermore, in the method disclosed in Patent Document 3, because impurities are observed visually, problems arise that a type of metal included in the impurities cannot be specified and a numerical value for an amount of contamination cannot be estimated.

(Patent Document 1) Japanese Unexamined Patent Application, First Publication No. H07-130808

(Patent Document 2) Japanese Unexamined Patent Application, First Publication No. 2000-35424

(Patent Document 3) Japanese Unexamined Patent Application, First Publication No. H11-330043

SUMMARY OF THE INVENTION

The present invention is conceived in order to solve the above described problems, and it is an object thereof to provide a method for analyzing impurities that measures a degree of impurity contamination in a surface of a silicon wafer and also measures a degree of impurity contamination of bulk portions of a silicon wafer.

A method for analyzing impurity of the present invention is a method for analyzing impurities present in a bulk layer of a silicon wafer, and the method includes: a step of immersing each of sets of two evaluation silicon wafers for obtaining evaluation data into a washing solution, thereby contaminating each of sets of the evaluation silicon wafers to be in a same state of contamination; a step of dissolving a surface layer portion of either one of the evaluation silicon wafers with a solution including hydrofluoric acid, and measuring a concentration of impurities included in the solution; a step of dissolving a bulk portion of the other evaluation silicon wafer with a solution including hydrofluoric acid, and measuring a concentration of impurities included in the solution; a step of determining a calibration curve that shows a relation between the concentrations of the impurities in the surface layer portions of the evaluation silicon wafers and the concentrations of the impurities in the bulk portions of the evaluation silicon wafers; a step of dissolving a surface layer portion of a silicon wafer of a test object which is immersed in the washing solution with a solution including hydrofluoric acid, and measuring a concentration of impurities included in the solution; and a step of determining a concentration of impurities in a bulk portion of the silicon wafer of a test object based on the calibration curve using the measured concentration of the impurities.

A diameter of the silicon wafer is not restricted. For example, a silicon wafer having a diameter of 150 mm (6 inches) may be used, or a silicon wafer having a diameter of 200 mm (8 inches) may be used.

Orientation, specific resistance, thickness, and the like of the silicon wafer are also not restricted.

The washing solution may be an acid etching solution or may be an alkaline etching solution. For example, a silicon wafer is flattened by the alkaline etching solution. As the alkaline etching solution, a potassium hydroxide (KOH) solution or a sodium hydroxide (NaOH) solution can be used. Impurities are contained in the alkaline etching solution. These impurities are metals such as, for example, at least one of Ni or Cu.

A plurality of sets of two evaluation silicon wafers are prepared so as to obtain evaluation data for determining a calibration curve. One of the two silicon wafers is used to measure Ni concentration in a surface layer portion of the silicon wafer. The other silicon wafer is used to measure Ni concentration in a bulk portion of the silicon wafer.

A method for measuring the Ni concentration in the surface layer portion or in the bulk portion is not restricted. For example, atomic absorption spectrometry may be used or inductively coupled plasma mass spectrometry may be used.

In the method for analyzing impurity of the present invention, at first, sets of two evaluation silicon wafers are prepared for obtaining the evaluation data. In addition, a plurality of washing solutions, for example, alkaline etching solutions are prepared such that each of the washing solution has a different degree of contamination. Each of the sets of two evaluation silicon wafers is then immersed in one of the plurality of alkaline etching solutions. Thereby, each of the sets of the two evaluation silicon wafers can be contaminated in a same state of contamination.

Next, a surface layer portion (i.e., a layer in range from a surface to a depth of 1 μm) of either one of the two evaluation silicon wafers is dissolved using, for example, hydrogen fluoride. Next, the dissolving solution is analyzed using, for example, atomic absorption spectrometry. As a result, a concentration of impurities in the surface layer portion of the evaluation silicon wafer can be measured.

Also, with respect to the remaining other evaluation silicon wafer which forms a pair together with the measured evaluation silicon wafer, an interior thereof is cleaved. The cleaved evaluation silicon wafer is then dissolved using a dissolving solution, and a concentration of impurities in the bulk portion which are dissolved in the dissolving solution is measured using, for example, inductively coupled plasma mass spectrometry.

The measurement of the surface layer portion and the measurement of the bulk portion are performed for each of a plurality of the sets of the evaluation silicon wafers which has a different degree of contamination. Subsequently, a relation between the concentration of the impurities in the surface layer portion of the silicon wafer and the concentration of the impurities in the interior portion (i.e., the bulk portion) of the silicon wafer, that is, a calibration curve is determined.

In a measurement of a silicon wafer of a test object, a concentration of impurities in a surface layer portion of the silicon wafer is measured. From a result of this measurement, a concentration of impurities in a bulk portion of the silicon wafer is determined based on the aforementioned calibration curve. Accordingly, the concentration of impurities in the bulk portion can be measured without the silicon wafer being destroyed.

In the method for analyzing impurity of the present invention, the washing solution may be an acidic etching solution or an alkaline etching solution.

In particular, greater degree of flattening of the silicon wafer surface can be obtained using the alkaline etching solution than that obtained using the acidic etching solution.

The surface layer portion may be a layer extending from a surface of the silicon wafer to a depth of 1 μm.

When the silicon wafer is subjected to a flattening processing using the alkaline etching solution, impurities contained in the alkaline etching solution are located at a high concentration particularly in a range from a surface to 1 μm in a depth direction of the silicon wafer. Ni concentration is reduced as a depth increases.

The impurities may be at least either one of Ni or Cu. For example, impurities contained in the alkaline etching solution are metals such as, for example, at least one of Ni or Cu.

In the present invention, the sets of two evaluation silicon wafers are prepared for obtaining the evaluation data. In addition, the alkaline etching solutions are prepared such that each of the alkaline etching solutions has a different degree of contamination. At first, each of the sets of two evaluation silicon wafers is immersed in one of the alkaline etching solutions. Next, the surface layer portion (i.e., a layer in a range from a surface to a depth of 1 μm) of the silicon wafer is dissolved using hydrogen fluoride. Thereafter, the dissolving solution is analyzed using atomic absorption spectrometry. As a result, the concentration of impurities in the layer in a range from the surface to a depth of 1 μm of the silicon wafer can be measured. Also, with respect to the other silicon wafer which forms a pair together with the measured silicon wafer, the interior thereof is cleaved. And the concentration of impurities in the interior of the cleaved silicon wafer is measured. A plurality of the sets of two silicon wafers are measured. As a result, the relation between the concentration of impurities in the surface layer portion of the silicon wafer and the concentration of impurities in the interior portion (i.e., the bulk portion) of the silicon wafer can be determined.

Next, the concentration of impurities in the surface layer portion of the silicon wafer of the test object is measured, and the concentration of impurities in the bulk portion of the silicon wafer is determined based on the aforementioned relation. This method avoids a need to cleave the silicon wafer for measuring the concentration of impurities in the bulk portion.

BRIEF DESCRIPTION THE DRAWINGS

FIG. 1 is a graph showing a relation between a Ni concentration in a surface layer portion and a Ni concentration in bulk portions present in a silicon wafer according to an example of the present invention.

DETAILED DESCRIPTION OF THE INVENTION

Examples of the present invention will now be described with reference to a figure.

EXAMPLE 1

At first, a plurality of NaOH aqueous solutions (alkaline etching solutions) are prepared such that each of them includes a different quantity of Ni. In addition, 20 sets of two evaluation silicon wafers for obtaining evaluation data. The two evaluation silicon wafers which form a pair are immersed into the NaOH aqueous solution at the same time, thereby contaminating the two evaluation silicon wafers to be in a same state of contamination. Each of 20 sets of two evaluation silicon wafers is immersed into one of the NaOH aqueous solutions each of which has a different quantity of Ni so as to contaminate.

The method used for the contamination involves placing the evaluation silicon wafers on a carrier made of fluororesin and then immersing this in the etching solution of which a temperature is 80° C. Note that, because Ni is uniformly dissolved in the alkaline etching solution, it is not necessary to stir the solution while the evaluation silicon wafers are immersed therein.

Next, one of the sample set of two evaluation silicon wafers is placed on a flat jig made of polytetrafluoroethylene (whose registered trademark is "Teflon" and referred to as PTFE), and 500 µl of HF (two percent by weight)/$H_2O_2$ (two percent by weight)/$H_2O$ is dripped at room temperature onto a front surface thereof in which a naturally oxidized film is formed. The dripped solution is then scanned over an entire surface of the evaluation silicon wafer. The naturally oxidized film is then removed from the front surface and a rear surface of the evaluation silicon wafer.

Next, 1.0 ml of a liquid mixture of HF and $HNO_3$ in a ratio of 4:6 (percent by weight) respectively is dripped onto the flat jig made of PTFE. The liquid mixture is then sandwiched between the etched surface of the evaluation silicon wafer and the PTFE jig. Thereby, a surface layer portion (i.e., a layer in a range from a surface to a depth of 1 µm) of the silicon wafer is dissolved. The solution after this dissolving is then recovered, and the impurities are analyzed using atomic absorption spectrometry (AAS) in a graphite furnace. Accordingly, analysis of impurities in the surface layer portion of the silicon wafer is performed. Namely, a measurement value (concentration (ppt)) measured by atomic absorption spectrometry is obtained.

The concentration of impurities in the surface layer portion of the evaluation silicon wafer (i.e., a layer in a range from a surface to a depth of 1 µm) is measured because impurities are located in the largest quantity in this portion. Because of this, this portion has a sufficient detection concentration for measuring the concentration of impurities.

Next, as a preprocessing, the other evaluation silicon wafer is cleaved into 3 to 5 g, and these are then placed in a PTFE beaker. The natural oxide film of this cleaved sample is then removed and the sample is washed at room temperature using HF (five percent by weight)/$HNO_3$ (five percent by weight)/HCl (five percent by weight)/$H_2O$. A solution including $HF:HNO_3:H_2SO_4$ (in a volume ratio of 2.5:1:1.5) for dissolving silicon and the washed cleaved sample are put in each of beakers and placed in a vapor phase decomposition vessel made of PTFE or polypropylene such that the solution is not in contact with the sample. Next, vapor of the liquid mixture of HF and $HNO_3$ is generated without applying heat or pressure. As a result, the cleaved sample reacted with the vapor and is dissolved. Diammonium silicon hexafluoride $((NH_4)_2SiF_6)$ which is left as a residue from the dissolving is put into a mixed solution which has a weight ratio for the $HF:HCl:HNO_3$ of 1:2:1 and of which a temperature is 150 to 220° C. so as to sublimate the residue. Next, in a liquid mixture of HF (two percent by weight)/$H_2O_2$ (two percent by weight)/$H_2O$ at room temperature, the residue including metal is dissolved and recovered, and Ni concentration in the bulk portion of the evaluation silicon wafer is measured using inductively coupled plasma mass spectrometer.

A graph is then made using the Ni concentrations measured from each of the evaluation silicon wafers in which the Ni concentrations (1) in the surface layer portions are taken as a horizontal axis and the Ni concentrations (2) in the bulk portions of the evaluation wafers are taken as a vertical axis so as to show a relation between those. The results are shown in FIG. 1.

Note that the Ni concentrations in the surface portions are determined using the calculation formula (A) shown below and values measured by atomic absorption spectrometry. Unit of the Ni concentration in the horizontal axis is atoms/$cm^2$.

$$\text{Ni concentration (atoms/cm}^2\text{)=concentration (ppt)} \times \text{volume (ml) of liquid mixture of HF/HNO}_3 \times 6.02 \times 10^{23} \text{(atoms/mol)} \div \text{Ni mass number (pg/mol)} \div (7.50^2 \times 3.14 \text{ cm}^2) \quad \text{formula (A)}$$

Here, concentration (ppt): a measured value obtained by atomic absorption spectrometry;

1 ppt=1 pg/ml;

$6.02 \times 10^{23}$ (atoms/mol): Avogadro's number;

Ni mass number (pg/mol)=$58.71 \times 10^{12}$ pg/mol; and $7.50^2 \times 3.14$ $cm^2$: surface area of a silicon wafer having a diameter of 150 mm.

The Ni concentration of the bulk portion shown on the vertical axis (2) is determined using the calculation formula (B) given below from values measured using inductively coupled plasma mass spectrometry. Unit of the Ni concentration in the vertical axis is atoms/$cm^3$.

$$\text{Ni concentration (atoms/cm}^3\text{)=concentration (ppt)} \times \text{volume (ml) of liquid mixture of HF/H}_2\text{O}_2\text{/H}_2\text{O} \times \text{total mass of silicon wafer (g)} \div \text{dissolved quantity of cleaved silicon wafer (g)} \div \text{thickness of silicon wafer (cm)} \times 6.02 \times 10^{23} \text{(atoms/mol)} \div \text{Ni mass number (pg/mol)} \div (7.50^2 \times 3.14 \text{ cm}^2) \quad \text{formula (B)}$$

Here, concentration (ppt): measured value obtained by inductively coupled plasma mass spectrometry;

1 ppt=1 pg/ml;

total mass of silicon wafer: 25.4 g; and thickness of silicon wafer: 0.0675 cm.

As a result, as shown in FIG. 1, a close linear relation between the measured Ni concentrations in the bulk portions (2) and the measured Ni concentrations in the surface portions (1), and a coefficient of correlation is 0.96. Accordingly, this linear relation is expressed as a function of $(2)=2057.3 \times (1)^{0.8793}$. From this linear relational expression, even in the case in which a method for measuring (2) is not applied, when the Ni concentration (1) in the surface layer portion is determined, the Ni concentration (2) in the bulk layer portion can be determined. Namely, when the Ni concentration of the surface layer portion is measured, then it is possible to calculate the Ni concentration of the bulk portion using the above described relational expression without actually cleaving the silicon wafer.

As a result of the above, the concentrations of Ni impurities in the surface layer portions and in the bulk portions of the evaluation silicon wafers for obtaining evaluation data are measured. And the linear relational expression showing the relation between those is then determined. Consequently, in an actual measurement, by measuring the Ni concentration of the surface layer portion, the concentration of the bulk portion can be determined. In an actual measurement for the bulk portion, there is no need to cleave the silicon wafer in order to measure the bulk portion.

What is claimed is:

1. A method of analyzing impurities in a bulk layer of a silicon wafer, the method comprising:

immersing each of sets of two evaluation silicon wafers into a washing solution to obtain evaluation data, thereby contaminating each of sets of the evaluation silicon wafers to be in a same state of contamination;

dissolving a surface layer portion of one of the evaluation silicon wafers with a solution including hydrofluoric acid, and measuring a concentration of impurities included in the solution;

dissolving a bulk portion of the other evaluation silicon wafer with a solution including hydrofluoric acid, and measuring a concentration of impurities included in the solution;

determining a calibration curve that characterizes a relation between the concentrations of the impurities in the surface layer portions of the evaluation silicon wafers and the concentrations of the impurities in the bulk portions of the evaluation silicon wafers;

dissolving a surface layer portion of a silicon wafer of a test object which is immersed in the washing solution with a solution including hydrofluoric acid, and measuring a concentration of impurities included in the solution; and determining a concentration of impurities in a bulk portion of the silicon wafer of a test object based on the calibration curve using the measured concentration of the impurities.

2. The method for analyzing impurity according to claim 1, wherein the washing solution is an acidic etching solution or an alkaline etching solution.

3. The method for analyzing impurity according to claim 1, wherein the surface layer portion is a layer extending from a surface of the silicon wafer to a depth of 1 μm.

4. The method for analyzing impurity according to claim 1, wherein the impurities are at least either one of Ni or Cu.

* * * * *